US006459772B1

(12) United States Patent
Wiedenhoefer et al.

(10) Patent No.: US 6,459,772 B1
(45) Date of Patent: Oct. 1, 2002

(54) RADIOGRAPHIC REFERENCE MARKER

(75) Inventors: Curt Wiedenhoefer, El Macero; Steven F. Glander, Davis; Stephen L. Gage, Wilton; Paul Katsch, Davis, all of CA (US)

(73) Assignee: Eisenlohr Technologies, Inc., Davis, CA (US)

( * ) Notice: Subject to any disclaimer, the term of this patent is extended or adjusted under 35 U.S.C. 154(b) by 0 days.

(21) Appl. No.: 09/527,845

(22) Filed: Mar. 17, 2000

Related U.S. Application Data

(60) Provisional application No. 60/124,945, filed on Mar. 18, 1999.

(51) Int. Cl.⁷ .......................... A61B 19/00; G01S 15/00
(52) U.S. Cl. ....................................... 378/163; 378/207
(58) Field of Search .......................... 378/163, 56, 205, 378/206, 207; 600/414

(56) References Cited

U.S. PATENT DOCUMENTS

| | | | |
|---|---|---|---|
| 2,109,780 A | | 3/1938 | Mott |
| 3,812,842 A | | 5/1974 | Rodriguez |
| 3,941,127 A | | 3/1976 | Froning |
| 4,028,545 A | * | 6/1977 | Foster ........................ 378/207 |
| 4,506,676 A | | 3/1985 | Duska |
| 5,149,965 A | * | 9/1992 | Marks ........................ 378/163 |
| 5,394,457 A | | 2/1995 | Leibinger et al. |
| 5,469,847 A | | 11/1995 | Zinreich et al. |
| 5,636,255 A | * | 6/1997 | Ellis ............................. 378/20 |
| 5,848,125 A | * | 12/1998 | Arnett ........................ 378/162 |

OTHER PUBLICATIONS

Peter M. Stevens, MD, "Radiographic Distortion of Bones: A Marker Study", *Orthopedics,* vol. 12, No. 11 (1989), pp. 1457–1463.

* cited by examiner

*Primary Examiner*—Drew Dunn
(74) *Attorney, Agent, or Firm*—Stevens, Davis, Miller & Mosher, LLP

(57) ABSTRACT

A radiographic reference marker which facilitates the accurate calculation of the degree of magnification or minification or minimization of radiographic images includes a reusable portion and a disposable portion. The reusable portion includes a radiopaque sphere of outside diameter $d_1$, and a radiolucent plastic housing capable of frictionally but removably engaging the sphere and including a plate attaching face and a housing attaching face. The plate attaching face includes in a center portion thereof an aperture of a diameter capable of allowing passage therethrough of the sphere, and the housing attaching face includes a first portion of a means for removably attaching the reusable portion to the disposable portion. The reusable portion also includes an attenuating plate having a first surface and a second surface, a thickness sufficient to attenuate radiation, and a component for removably attaching the second surface of the attenuating plate to the plate attaching face of the plastic housing. The disposable portion includes a mounting substrate having a substrate attaching face and a mounting face, and the substrate attaching face includes a second portion of the component for removably attaching the reusable portion to the disposable portion. The mounting face also includes a component for removably attaching the mounting substrate to a subject.

21 Claims, 7 Drawing Sheets

RADIOGRAPHIC REFERENCE MARKER

This application claims the priority of U.S. Provisional Application No. 60/124,945 filed Mar. 18, 1999, and incorporated herein by reference.

BACKGROUND OF THE INVENTION

1. Field of the Invention

This invention relates generally to a method for the determination of the degree of magnification or minification or minimization of radiographic images. The invention relates more specifically to a method and apparatus capable of facilitating the accurate calculation of the degree of magnification or minification or minimization of radiographic images.

2. Discussion of the Prior Art

In the interpretation of radiographic images, various approaches are known for differentiating between structures which appear in such images. For example, U.S. Pat. No. 2,109,780 describes a shoe fitting device in which a marker of an opaque material which is impermeable to x-ray radiation is used to distinguish between the fleshy parts of the foot and the contiguous parts of a shoe upper.

Furthermore, various approaches are known which serve to locate anatomical structures in the radiographic images of the human body. For example, U.S. Pat. No. 4,506,676 describes an adhesive, flexible tape which includes radiopaque dots. The tape is applied to a patient to identify an area of interest, and the image of the dot appears in the x-ray photograph as a pointer to the area.

U.S. Pat. No. 3,812,842 describes an indexing scale which includes markers that are visible in x-ray photographs. The markers facilitate locating a particular blood vessel relative to the scale in the x-ray photograph, and the arms which support the indexing device are secured to a patient's chest with adhesive tape.

U.S. Pat. No. 5,394,457 describes a device for marking body sites for imaging medical examinations. By using multiple markers, two x-ray exposures taken from different directions can be used to determine the spatial location of any desired point. The marker has a head with a cavity for receiving a substance which exhibits high contrast, and in one embodiment, the fixture which supports the marker is attached to the skin with an adhesive.

U.S. Pat. No. 5,469,847 describes an adhesive surface marker with a cavity for receiving imaging materials. The surface marker contains an x-ray opaque gel, such as barium sulfate, which is sealed on all sides by an outer casing. The use of multiple markers provides reference points which allow the geometrical calculation of the precise location of a particular site within a patient's body.

The assessment of radiographic images, however, must account for image distortion caused by parallax and magnification or minification or minimization (hereinafter referred to as "magnification") artifact. That is, magnification artifact introduces a source of error into the measurement of linear distances in radiographic images. Thus, while use of an apparatus such as that described in U.S. Pat. No. 5,469,847 will allow the geometrical calculation of the precise location of a particular site, the image of the distance from any one marker to another marker is always magnified to some extent.

U.S. Pat. No. 3,941,127 describes a device that is placed in the same plane as the anatomical object of interest in order to correct for magnification distortion. A radiopaque interval marker reference is placed adjacent to the torso of a patient at a distance from the film so as to make equal magnification distortion between the markings on the reference and the plane of the patient's torso.

To determine the actual distance from one location in an image to another location in an image, however, the true degree of magnification must be known. One approach to providing a method of calculating the degree of magnification employs an apparatus with two small lead spheres encased in plastic and spaced 100 mm apart (made by Osteonics, Inc., Allendale, N.J.). Although Osteonics discloses the possible necessity of wrapping one or both ends of the apparatus with led foil to improve the metallic sphere visibility on an x-ray, the device has neither an attenuating plate, nor adhesive to facilitate attachment of the device to a patient. In such a two-point, but one-dimensional device, the potential exists for underestimation of the magnification artifact. If the two points are not in a plane exactly parallel to the radiographic film, the apparent distance between the spheres will decrease and appear shorter on the image, thereby making it impossible to accurately calculate the degree of magnification.

In order to overcome the limitation associated with the aforementioned two-point marker, an apparatus employing a flat plate of standard metal with three small lead spheres the size of a BB pressed into 1.5 mm holes spaced in a 40 mm equilateral triangle configuration (made by Ortho-Graphics, Inc., Salt Lake City, Utah) is described in Stevens, P. M., "Radiographic Distortion of Bones: A Marker Study," Orthopedics, Vol. 12, No. 11 (1989), pp. 1457–1462. Though acknowledging the hypothetical superiority of a spherical marker, the reference dismisses it as being both too heavy and awkward to secure to a patient, and capable of casting a shadow with a fuzzy perimeter, making measurement imprecise. While one side of the three-point device has a 90°-bend with a 1 cm flat surface that is applied to a patient, the device has no self-adhesive, and is very difficult to attach. Though the flat plate does help to sharpen the image of the small spheres, the three points are all located in the same plane. As with the aforementioned two-point device, if the three points are not all in a plane exactly parallel to the radiographic film, the apparent distance between the spheres will decrease and appear shorter on the image, thereby making it impossible to accurately calculate the degree of magnification.

Thus, while each of the latter devices may provide an assessment of the distortion in radiographic images, because the two or three points are all located in one plane, neither of these devices is capable of providing a truly reliable, accurate assessment of the degree of magnification. Furthermore, while the three-point device may be directionally somewhat more accurate than the two-point device, the inability to easily and quickly attach it to and detach it from a patient diminishes its attractiveness.

Therefore, a general need exists to provide the radiographical profession with a method for the accurate determination of the degree of magnification of radiographic images. A more specific need exists for a method and apparatus capable of facilitating the accurate calculation of the degree of magnification of radiographic images which is both less sensitive to the orientation of the marker relative to the beam of radiation, and easily mounted on and detached from a subject.

SUMMARY OF THE INVENTION

It is an object of the present invention to provide a method and apparatus capable of facilitating the accurate calculation of the degree of magnification of radiographic images (including digital and analog radiographic images). The description below is generally in the context of developed analog radiographic images made on X-ray film with a conventional X-ray machine but it will be understood that the images would be essentially the same if the images were made digitally using a digital radiation detector also known as a digital X-ray machine.

Accordingly, the present invention advantageously relates to a radiographic reference marker which satisfies each of the aforementioned criteria. In a preferred embodiment, the reference marker comprises a reusable portion and a disposable portion. The reusable portion comprises a radiopaque sphere of outside diameter $d_1$, and a radiolucent plastic housing capable of engaging the sphere and comprising a plate attaching face and a housing attaching face. The plate attaching face comprises in a center portion thereof an aperture of a diameter capable of allowing passage therethrough of the sphere, and the housing attaching face comprises a first portion of a means for removably attaching the reusable portion to the disposable portion. The reusable portion also comprises an attenuating plate having a first surface and a second surface, a thickness sufficient to attenuate radiation, and a means for removably attaching the second surface of the attenuating plate to the plate attaching face of the plastic housing. The disposable portion comprises a mounting substrate having a substrate attaching face and a mounting face, and the substrate attaching face comprises a second portion of the means for removably attaching the reusable portion to the disposable portion. The mounting face comprises a means for removably attaching the mounting substrate to a subject.

The invention further relates to a radiographic reference marker which facilitates the accurate calculation of the degree of magnification or minification or minimization of radiographic images which includes a reusable portion and a disposable portion. The reusable portion includes a radiopaque sphere of outside diameter $d_1$, and a radiolucent plastic housing capabable of frictionally but removably engaging the sphere and including a plate attaching face and a housing attaching face. The plate attaching face includes in a center portion thereof an aperture of a diameter capable of allowing passage therethrough of the sphere, and the housing attaching face includes a first portion of a means for removably attaching the reusable portion to the disposable portion. The reusable portion also includes an attenuating plate having a first surface and a second surface, a thickness sufficient to attenuate radiation, and a means for removably attaching the second surface of the attenuating plate to the plate attaching face of the plastic housing. The disposable portion includes a mounting substrate having a substrate attaching face and a mounting face, and the substrate attaching face includes a second portion of the means for removably attaching the reusable portion to the disposable portion. The mounting face includes a means for removably attaching the mounting substrate to a subject. The reference marker is employed by attaching the reusable portion to the disposable portion, affixing the attached reusable portion and disposable portion to a subject, and irradiating a radiographic film to produce a first image of diameter $d_2$ and a second shadow image disposed concentrically around the first image. Once diameter $d_2$ has been measured, comparison of measured image diameter $d_2$ with known sphere diameter $d_1$ enables one to accurately calculate the degree of the magnification or minification of the radiographic image.

The invention further relates to a method of calculating the degree of magnification of radiographic images. The reference marker is employed by affixing the disposable portion to a subject, attaching the reusable portion to the disposable portion, and irradiating a radiographic film to produce both a first image of outside diameter $d_2$ and a second shadow image, i.e., a graying effect, disposed concentrically around the first image. Once diameter $d_2$ has been measured, comparison of measured image diameter $d_2$ with known sphere diameter $d_1$ enables one to accurately calculate the degree of magnification of the radiographic image.

The advantages associated with the present reference marker are numerous. First, by virtue of its use of a spherical reference point, it overcomes the limitation associated with one-dimensional devices, and provides for the accurate calculation of the degree of magnification of an image. By employing the attenuating plate in conjunction with the uniform plastic housing, the marker produces the uniform secondary shadowing around the more dense material of the sphere. Finally, by virtue of its self-adhesive means for attaching to a subject, the marker is easily mounted on and detached from a subject.

BRIEF DESCRIPTION OF THE DRAWING

Other objects, features, and advantages of the present invention will become more fully apparent from the following detailed description of the preferred embodiments, the appended claims, and the accompanying drawings. As depicted in the attached drawings:

DESCRIPTION OF THE PREFERRED EMBODIMENTS

The present invention will be disclosed in terms of the currently perceived preferred embodiments thereof.

Figure 1:
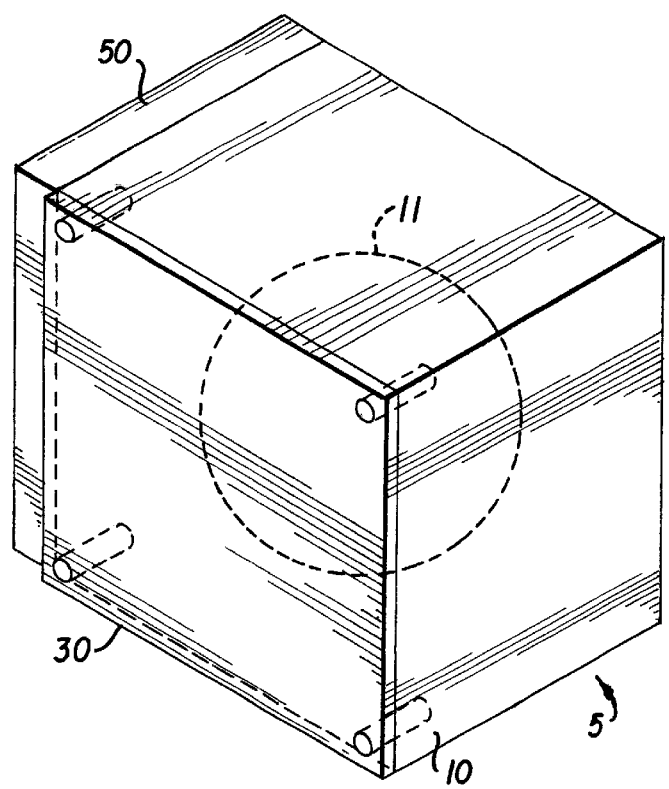
FIG. 1 is a perspective view of a radiographic reference marker constructed in accordance with the teachings of a first preferred embodiment of the present invention.

Referring to FIG. 1, a radiographic reference marker 5 constructed in accordance with a first preferred embodiment of the present invention is shown. The radiographic reference marker 5 comprises a reusable portion 10 and a disposable portion 50. Reusable portion 10 is temporarily attached to disposable portion 50, and disposable portion 50 is temporarily mounted on a subject, during that period of time when a radiographic film is being exposed.

Figure 2:
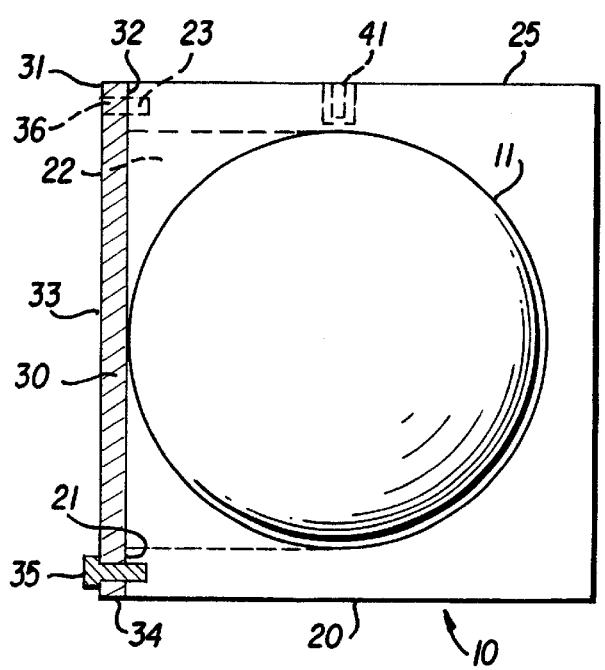
FIG. 2 is a top sectional view of a reusable portion of the radiographic reference marker constructed in accordance with the teachings of the first preferred embodiment of the present invention.

As depicted in FIG. 2, the reusable portion 10 comprises a radiopaque sphere 11 having an outside diameter "$d_1$" of from approximately 1 mm to 100 mm, with $d_1$ typically being from approximately 20 mm to 40 mm, and even more typically approximately 30 mm. The sphere can be either hollow or solid but in view of weight considerations, is preferably hollow. In a preferred embodiment, the material of construction of sphere 11 is brass.

The sphere 11 is frictionally but removably engaged in a radiolucent plastic housing 20 which comprises a plate attaching face 21 and a housing attaching face 25. Plate attaching face 21 comprises in a center portion thereof an aperture 22 of a diameter capable of allowing passage therethrough of sphere 11 of diameter $d_1$.

Figure 3:
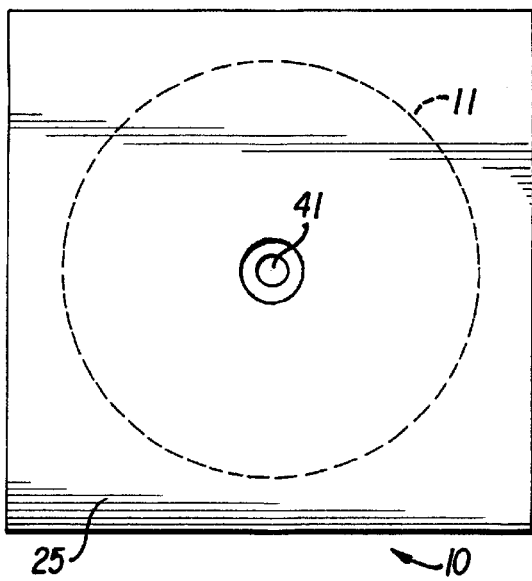
FIG. 3 is a side elevational view of the reusable portion of the radiographic reference marker constructed in accordance with the teachings of the first preferred embodiment of the present invention.

As depicted in FIGS. 2 and 3, housing attaching face 25 of plastic housing 20 comprises a first portion 41 of a means for removably attaching the reusable portion 10 to the disposable portion 50. In this preferred embodiment, the means for removably attaching is a metal snap assembly, but other possible embodiments include any means which provides a secure but easily detachable connection between the reusable portion 10 and the disposable portion 50.

As depicted in FIG. 3, in this preferred embodiment, the first portion 41 of the means for removably attaching is the female portion of the snap assembly. The female portion of the snap assembly is embedded into the center of housing attaching face 25 of plastic housing 20.

Figure 6:
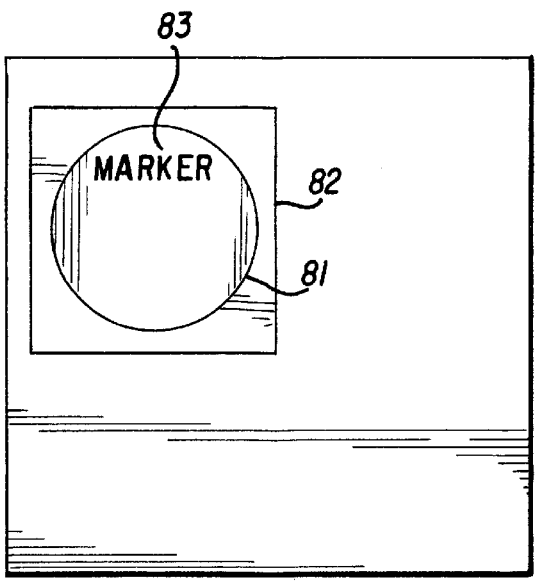
FIG. 6 is a front elevational representation of an x-ray photograph depicting the magnified image of a sphere element of the radiographic reference marker.

As depicted in FIG. 2, reusable portion 10 further comprises an attenuating plate 30, which in a preferred embodiment is of metal construction and is substantially square in shape, comprising a first surface 31 (i.e., radiation-facing surface) and a second surface 32, the plane of which is parallel to the plane of first surface 31. Attenuating plate 30 has an edge 33 length of from approximately 20 mm to 40 mm, with an edge length of approximately 30 mm being preferred. Attenuating plate 30 has a thickness 34 between first surface 31 and a second surface 32 sufficient to attenuate radiation. A preferred thickness 34 is from approximately 0.5 to 3 mm, with a thickness of approximately 1 to 2 mm being more preferred. Attenuating plate 30 extends beyond the perimeter of the sphere 11 so as to attenuate the radiographic signal. This attenuation, as depicted in FIG. 6, produces both a sharper and clearer image 81 of sphere 11, and a secondary shadow image 82 (i.e., a graying effect), disposed concentrically around the sphere, on the radiographic film. The second surface 32 of attenuating plate 30 either is in contact with, or is in very close proximity to, the outer surface of sphere 11 which is exposed through aperture 22, so that the plate will still properly attenuate the radiation, even if the plate is not oriented perpendicular to the beam of radiation.

In an optional embodiment, first surface 31 of attenuating plate 30 can be etched and/or have applied (e.g., by means of a stencil) designs and/or alphabetic and/or numerical characters which appear as images 83 within the circumference of image 81 on the irradiated radiographic film (see FIG. 6). In another embodiment, second surface 32 of attenuating plate 30 can be etched and/or have applied (e.g., by means of a stencil) designs and/or alphabetic and/or numerical characters which would appear as images on the irradiated radiographic film.

In another embodiment, attenuating plate 30 could be etched so as to provide a continuous open space from first surface 31 through second surface 32. Alternatively, attenuating plate 30 could be etched so as to provide a continuous open space from first surface 31 to a point intermediate between first surface 31 and second surface 32.

The outer portions of first surface 31 or second surface 32 of attenuating plate 30 can also be etched and/or have applied designs and/or alphabetic and/or numerical characters in a manner as described above so as to cause the image or images of the etched and/or applied item or items to appear outside the circumference of the sphere on the irradiated radiographic film.

The contrast of the image or images of the etched and/or applied item or items on the irradiated radiographic film can be adjusted by adjusting the radio opacity of the etched and/or applied area as, for example but not by way of limitation, by filling the etched or, in the case of the applied material embodiment, the stenciled area, with a material which has a radio opacity between zero (0) and one (1) where material with radio opacity zero (0) allows total transmission of X-rays and where material with radio opacity one (1) totally blocks X-rays from the beam source to the X-ray film.

Attenuating plate 30 and plastic housing 20 further comprise a means for removably attaching the second surface 32 of the attenuating plate to the plate attaching face 21 of the plastic housing, such as, for example, a coating of an adhesive or threaded fasteners. In an embodiment in which threaded fasteners are employed, the threaded fasteners 35 penetrate apertures 36 in attenuating plate 30 to engage threaded cavities 23 in plate attaching face 21.

Figure 4:
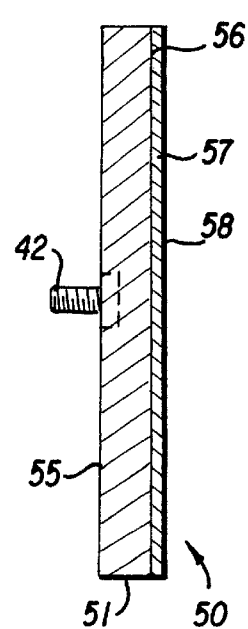
FIG. 4 is a vertical sectional view of a disposable portion of the radiographic reference marker constructed in accordance with the teachings of the first preferred embodiment of the present invention.
Figure 5:
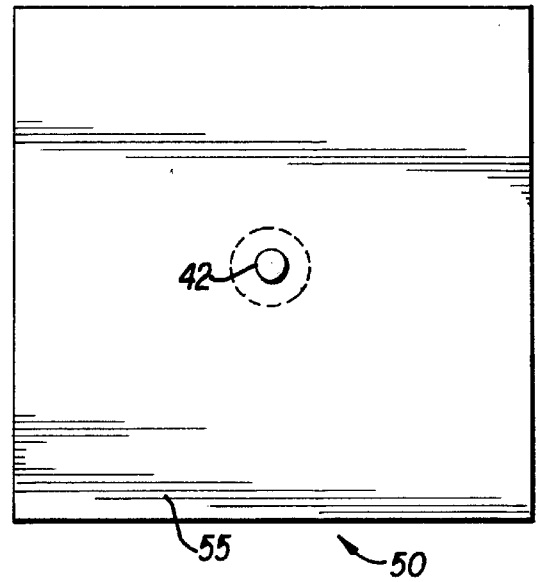
FIG. 5 is a front elevational view of the disposable portion of the radiographic reference marker constructed in accordance with the teachings of the first preferred embodiment of the present invention.

As depicted in FIG. 4, disposable portion 50, which functions as a subject interface, facilitates the reuse of reusable portion 10 with a plurality of subjects. Disposable portion 50 comprises a mounting substrate 51, such as, for example, a foam pad, having an edge length of approximately 30 mm. As depicted in FIGS. 4 and 5, substrate attaching face 55 of mounting substrate 51 comprises a second portion 42 of a means for removably attaching the reusable portion 10 to the disposable portion 50. In this preferred embodiment, the second portion 42 of the means for removably attaching is the male portion of the snap assembly. The male portion of the snap assembly is embedded into the center of substrate attaching face 55 of mounting substrate 51 so that the long axis of the male portion is oriented perpendicular to the plane of substrate attaching face 55.

Disposable portion 50 further comprises a mounting face 56 which facilitates attachment of the mounting substrate 51 to a subject. Mounting face 56 comprises a means 57 for removably attaching mounting substrate 51 to the subject, such as, for example, a coating of an adhesive. A covering 58 is removably affixed to means 57 for removably attaching, and covering 58 is removed prior to attaching mounting substrate 51 to the subject.

The method of employing radiographic reference marker 5 comprises the following series of steps. First, reusable portion 10 is removably attached to disposable portion 50 by attaching first portion 41 of the means for removably attaching to the second portion 42 of the means for removably attaching. Then, mounting face 56 of the mounting substrate 51 of disposable portion 50 is removably affixed to a subject, thereby mounting the attached reusable portion lo and disposable portion 50 of reference marker 5. The reference marker 5 is affixed such that first surface 31 of attenuating plate 30 and the surface of the subject to be irradiated, such as, for example, with radiation of x-ray wavelength, are located substantially equidistant from an unexposed radiographic film, and such that first surface 31 of attenuating plate 30 is oriented substantially perpendicular to the beam path of the radiation. Next, the radiographic film is irradiated to produce on the irradiated radiographic film a first image 81 of diameter "$d_2$" (see FIG. 6). As result of the attenuation of the radiographic signal by attenuating plate 30, the irradiated radiographic film also includes second shadow image 82 disposed concentrically around image 81 (see FIG. 6). This secondary shadowing produces both a sharper and clearer image 81 of sphere 11.

Reusable portion 10 is then detached from disposable portion 50 by separating first portion 41 of the means for removably attaching from the second portion 42 of the means for removably attaching. Reusable portion IO can then be reused in subsequent exposures. Mounting face 56 of disposable portion 50 is separated from the subject, and disposable portion 50 is then discarded.

FIG. 6 is a front elevational representation of an x-ray photograph depicting the magnified first image 81 of sphere 11, and the second shadow image 82 disposed concentrically around image 81. Since the embodiment of the invention depicted in FIG. 6 is based upon the aforementioned first preferred embodiment of the shape of attenuating plate 30 (i.e., substantially square in shape), the perimeter of second shadow image 82 is substantially square in shape. Image 81 on the irradiated radiographic film is then measured to determine the diameter $d_2$. By comparing the measured image diameter $d_2$ with known sphere diameter $d_1$, one can calculate the percentage of magnification "M" of the radiographic image as follows:

$$M = \frac{d_2 - d_1}{d_1} \times 100\%.$$

If the value of $d_2$ is less than the value of $d_1$, the difference is multiplied by −1 to obtain a positive value for the percentage of minification or minimization.

Figure 7:
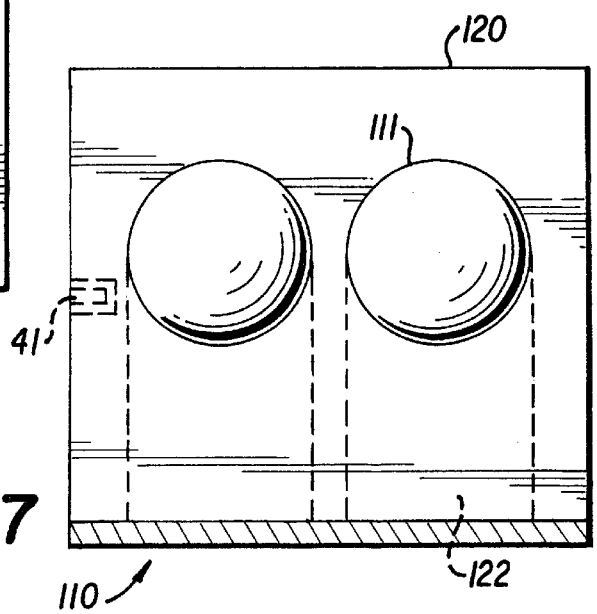
FIG. 7 is a top sectional view of a radiographic reference marker constructed in accordance with the teachings of a second preferred embodiment of the present invention in which first and second spheres are located in a single housing.

Referring to FIG. 7, reusable portion 110 of a radiographic reference marker constructed in accordance with a second preferred embodiment of the present invention is shown. In this embodiment, in which attenuating plate 30 and means for removably attaching the second surface 32 of the attenuating plate to the plate attaching face 21 of the plastic housing are as set forth above, first and second spheres 111 are located in first and second apertures 122 in a single housing 120.

Figure 8:
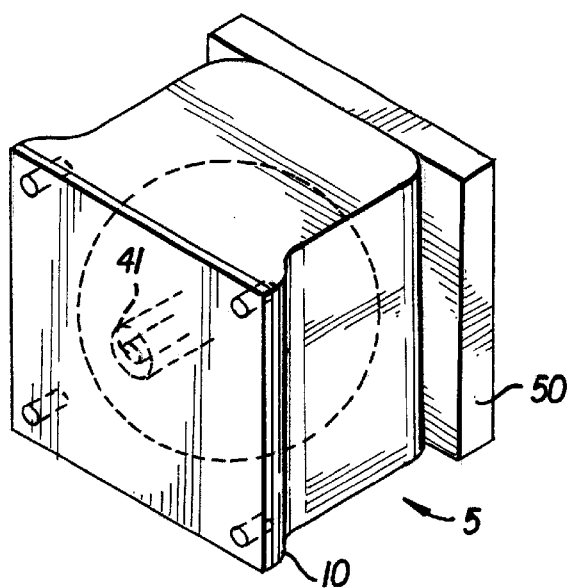
FIG. 8 is a perspective view of a radiographic reference marker constructed in accordance with the teachings of a third preferred embodiment of the present invention.

FIG. 8 is a perspective view of a radiographic reference marker constructed in accordance with the teachings of a third preferred embodiment of the present invention. In the first preferred embodiment of the reference marker depicted in FIG. 1, the first surface 31 (i.e., radiation-facing surface) of attenuating plate 30 of reusable portion 10 is oriented perpendicularly to the substrate attaching face 55 of disposable portion 50. In the third preferred embodiment of the reference marker as depicted in FIG. 8, the first surface 31 of attenuating plate 30 of reusable portion 10 is oriented parallel to the substrate attaching face 55 of disposable portion 50. This orientation facilitates the mounting of one or a plurality of reference markers to a self-supporting stand 310 as depicted in FIG. 10.

Figure 9:
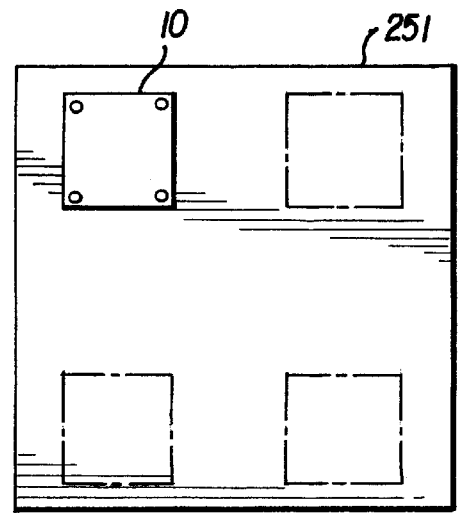
FIG. 9 is a front elevational view of a radiographic reference marker assembly constructed in accordance with the teachings of the third preferred embodiment of the present invention in which a plurality of single-sphere reusable portions are attachable to a single mounting substrate.

Referring to FIG. 9, a radiographic reference marker assembly 204 constructed in accordance with a third preferred embodiment of the present invention is shown. In this embodiment, a plurality of single-sphere reusable portions 10 are attachable to a single mounting substrate 251.

Figure 10:
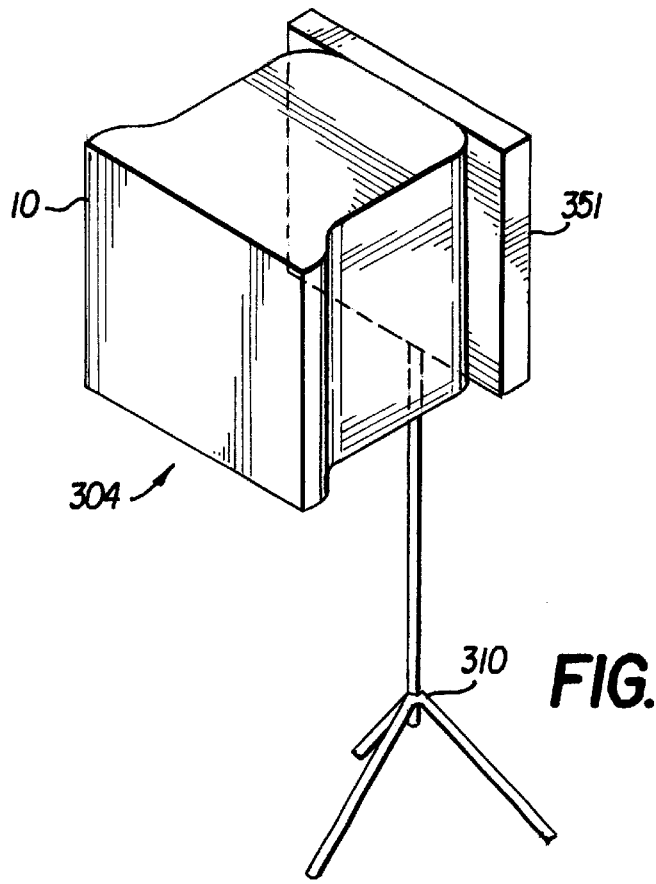
FIG. 10 is a perspective view of a radiographic reference marker assembly constructed in accordance with the teachings of a fourth preferred embodiment of the present invention in which one or a plurality of reusable portions are attachable to a mounting substrate which is attachable to a self-supporting stand.

Referring to FIG. 10, a radiographic reference marker assembly 304 constructed in accordance with a fourth preferred embodiment of the present invention is shown. In this embodiment, reference marker assembly 304 comprises a mounting substrate 351 to which one or a plurality of reusable portions 10 can be attached, with mounting substrate 351 attachable to self-supporting stand 310. Reference marker assembly 304 is movable, and can be situated in close proximity to the object to be irradiated.

Figure 11:
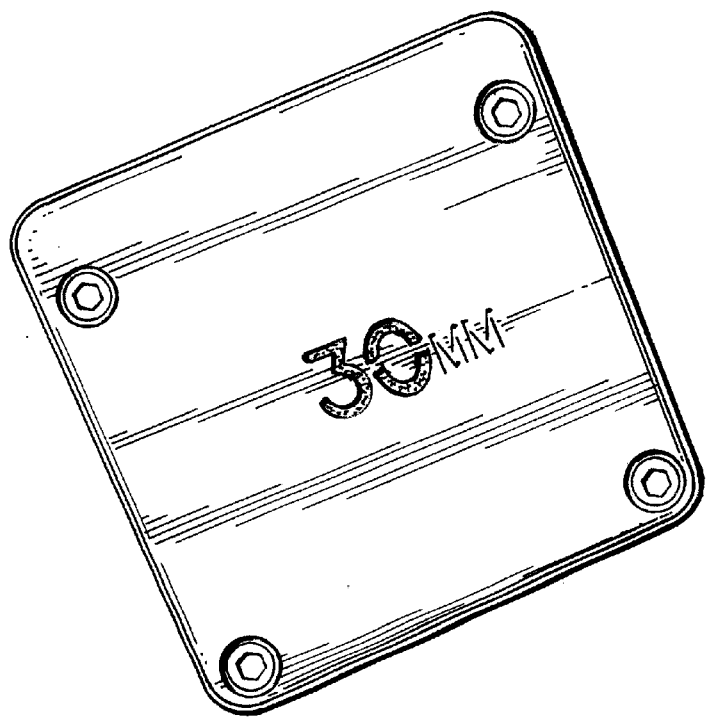
FIG. 11 is a photograph of the radiation-facing surface of the attenuating plate of the radiographic reference marker.

FIG. 11 is a photograph of the first surface 31 (i.e., radiation-facing surface) of the attenuating plate 30 of the radiographic reference marker.

Figure 12:
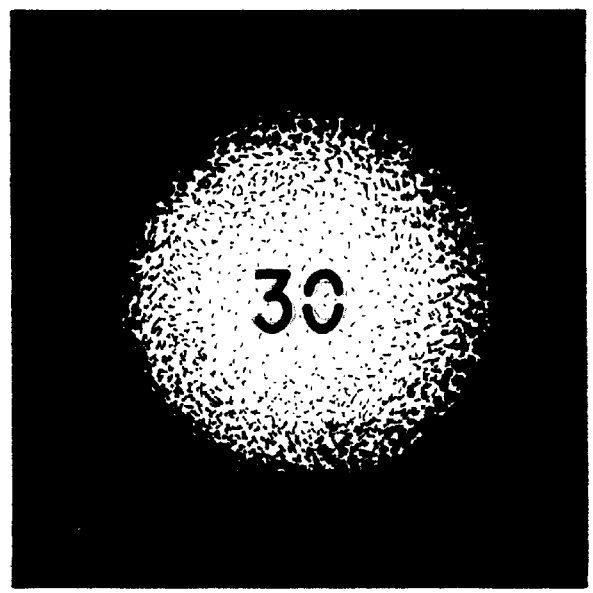
FIG. 12 is a photograph of the developed x-ray image of a sphere element of the radiographic reference marker.

FIG. 12 is a photograph of the developed x-ray image of sphere 11 of the radiographic reference marker. The photograph illustrates first image 81 of sphere 11, and the second shadow image 82 disposed concentrically around image 81.

Figure 13:
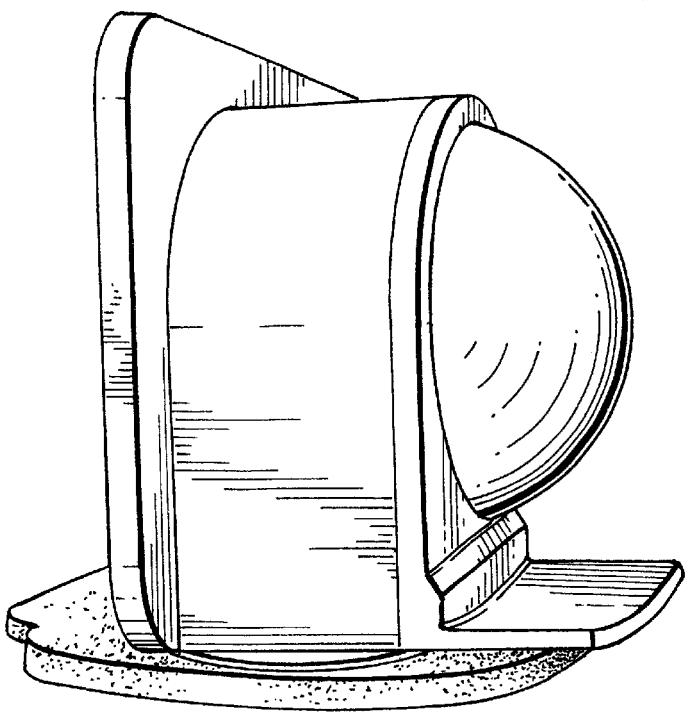
FIG. 13 is a side view photograph of the radiographic reference marker in which the radiation-facing surface of the attenuating plate of the reusable portion is oriented perpendicularly to a substrate attaching face of the disposable portion.

FIG. 13 is a side view photograph of the radiographic reference marker according to another preferred embodiment. In this embodiment, the first surface 31 (i.e., radiation-facing surface) of attenuating plate 30 of reusable portion 10 is oriented perpendicularly to the substrate attaching face 55 of disposable portion 50. While the orientation of reusable portion 10 relative to substrate attaching face 55 is the same as that in the first preferred embodiment described herein (FIG. 1), in this embodiment, the sphere 11, rather than being fully enclosed in a housing such as plastic housing 20, is only partially enclosed. That is, the interior of the housing comprises a cavity with a beveled outer edge having a diameter slightly smaller than the diameter of sphere 11. The beveled outer edge and the cavity are capable of frictionally but releasably engaging sphere 11 within the housing.

Figure 14:
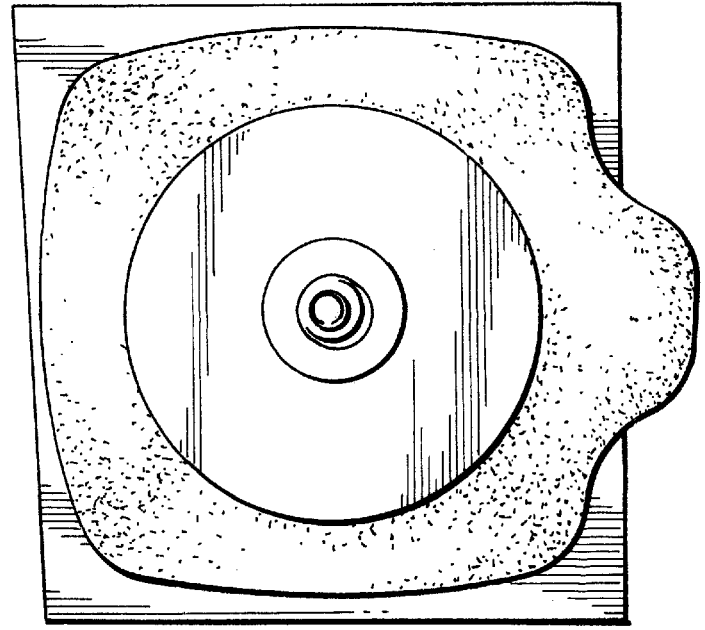
FIG. 14 is a photograph of the substrate attaching face of the disposable portion of the radiographic reference marker.

FIG. 14 is a photograph of the substrate attaching face 55 of the disposable portion 50 of the radiographic reference marker, and depicts the aforementioned second portion 42 (i.e., male portion) of the means for removably attaching (i.e.,a snap assembly in a preferred embodiment).

Figure 15:
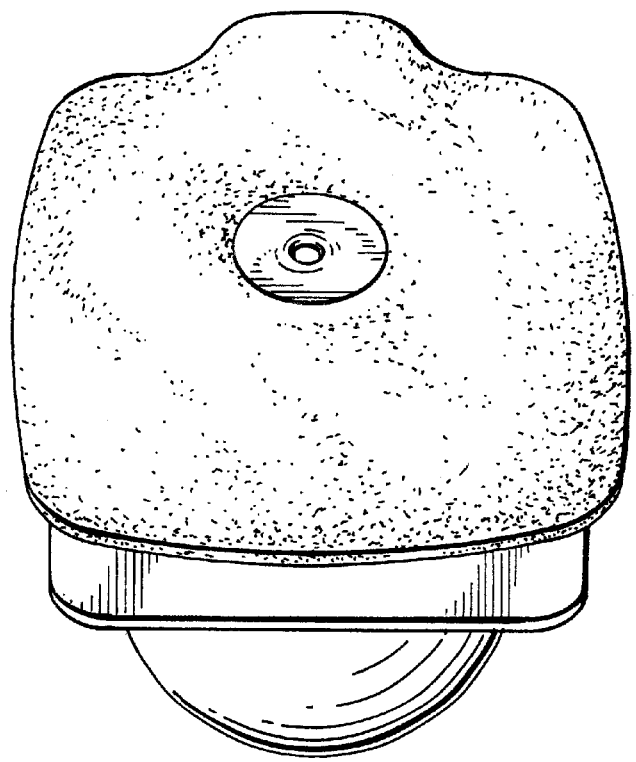
FIG. 15 is a photograph of the mounting face of the disposable portion of the radiographic reference marker.

FIG. 15 is a photograph of the mounting face 56 of the disposable portion 50 of the radiographic reference marker.

Figure 16:
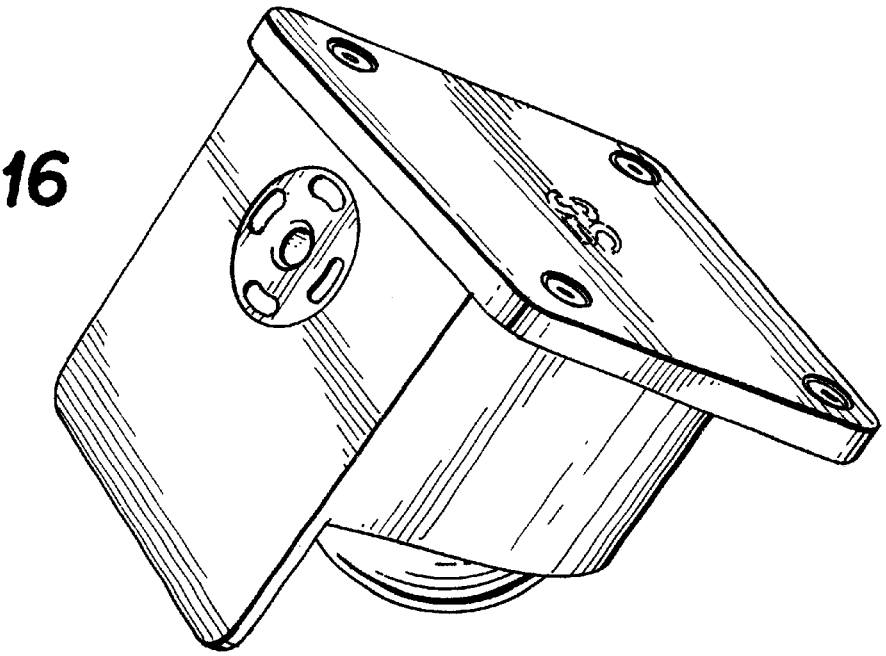
FIG. 16 is a perspective view photograph of the radiographic reference marker depicted in FIG. 13.

FIG. 16 is a perspective view photograph of the radiographic reference marker depicted in FIG. 13.

Figure 17:
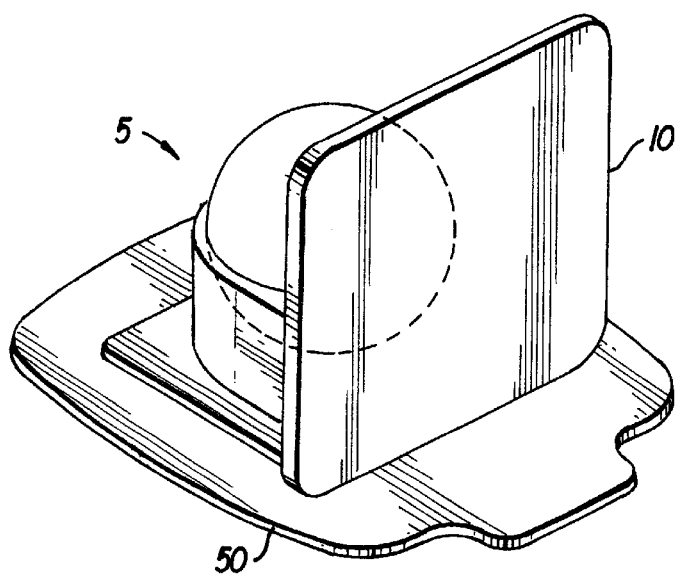
FIG. 17 is a perspective view of the radiographic reference marker depicted in FIG. 13.

FIG. 17 is a perspective view of the radiographic reference marker depicted in FIG. 13.

Figure 18:
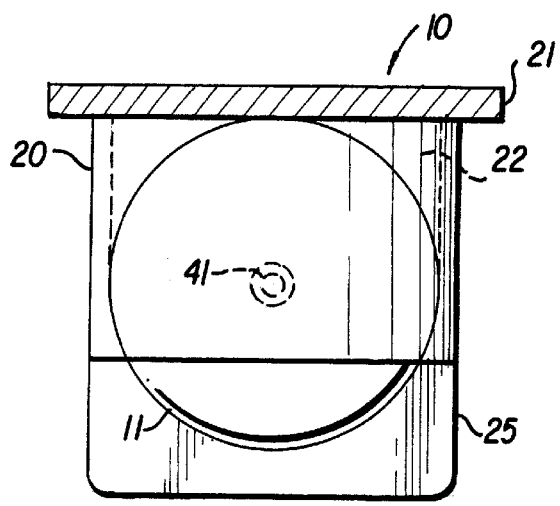
FIG. 18 is a sectional view of the radiographic reference marker depicted in FIG. 13.

FIG. 18 is a sectional view of the radiographic reference marker depicted in FIG. 13.

Figure 19:
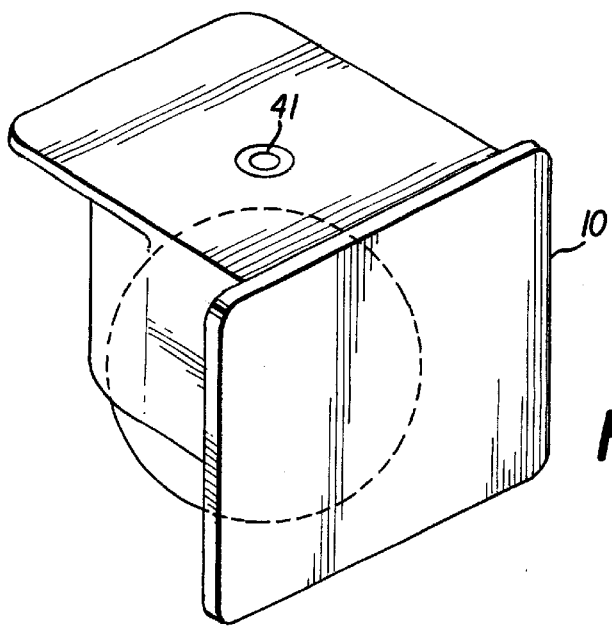
FIG. 19 is another perspective view of the radiographic reference marker depicted in FIG. 13.

FIG. 19 is another perspective view of the radiographic reference marker depicted in FIG. 13.

EXAMPLE

A reference marker having a sphere with an outside diameter $d_1$ of 25 mm was exposed to x-ray radiation. The diameter $d_2$ of the image of the sphere on the irradiated x-ray film was measured, and was determined to have a diameter of 30 mm. The percentage of magnification M of the radiographic image was then calculated as follows:

$$M = \frac{30-25}{25} \times 100\% = 20\%.$$

The present invention, therefore, provides a radiographic reference marker capable of facilitating the accurate calculation of the degree of magnification of radiographic images. By virtue of its use of a spherical reference point, it overcomes the limitation associated with conventional one-dimensional devices, and by employing the attenuating plate in conjunction with the uniform plastic housing, it produces a uniform secondary shadowing around the more dense material of the sphere. Finally, with its self-adhesive means for attaching to a subject, the marker is easily mounted on and detached from a subject.

The foregoing sets forth only one embodiment and alternative embodiments of a radiographic reference marker. Obviously, other embodiments can be designed within the scope of this invention.

It is to be understood that while the various aspects of the invention have been described above with respect to their preferred embodiments, other embodiments within the scope and spirit of this invention are possible.

For example, the marker has been described as comprising a radiopaque sphere 11 and attenuating plate 30, with the plate being provided for the purpose of attenuating the radiation. It should be appreciated, however, that the invention comprehends other configurations of attenuating material capable of providing a sharper image of the radiopaque sphere. For example, attenuating plate 30 could be eliminated, and the sphere could be coated with a material capable of attenuating the radiation.

By way of further example of modifications within the scope of this invention, sphere 11 has been described as having an outside diameter "$d_1$" of from approximately 1 mm to 100 mm. A sphere having an even smaller diameter could be employed, however, as long as the resultant image could be easily measured, and a sphere having an even larger diameter could be employed, as long as the associated larger overall marker could still be easily mounted on and detached from a subject.

By way of further example of modifications within the scope of this invention, sphere 11 has been described as being of brass construction in a preferred embodiment. Instead of being brass, however, the sphere could comprise, for example, any other material of construction which both is radiopaque and provides a suitable developed image.

By way of further example of modifications within the scope of this invention, attenuating plate 30 has been described as being substantially square in shape in a preferred embodiment. Instead of being square, however, the attenuating plate could be, for example, substantially circular or any other shape capable of extending beyond the diameter of sphere 11 and attenuating the radiation. In view of this, the shape of second shadow image 82 will be determined by the particular shape of the attenuating plate employed.

By way of further example of modifications within the scope of this invention, attenuating plate 30 has been described as being of metal construction in a preferred embodiment. Instead of being metal, however, the attenuating plate could comprise, for example, any other material of construction which both provides suitable attenuation of radiation and is capable of being formed into the necessary shape.

By way of further example of modifications within the scope of this invention, plastic housing 20 has been described as being of a shape capable of frictionally but removably engaging sphere 11 of outside diameter $d_1$. The housing could be, for example, substantially cube-shaped, cylindrical, or any other shape capable of frictionally but removably engaging sphere 11 as long as it is capable of attaching to attenuating plate 30 and has at least one face capable of mounting the marker on the subject.

By way of further example of modifications within the scope of this invention, attenuating plate 30 and plastic housing 20 have been described as comprising a means for removably attaching the second surface 32 of the attenuating plate to the plate attaching face 21 of the plastic housing, such as, for example, with a coating of an adhesive or threaded fasteners. Non-threaded fasteners, however, such as a smooth peg capable of frictionally but securely engaging a non-threaded cavity, could be employed.

By way of further example of modifications within the scope of this invention, attenuating plate 30 has been described as having a thickness 34 between first surface 31 and a second surface 32 sufficient to attenuate radiation. The thickness of the attenuating plate is of course dependent upon both the material from which the plate is constructed, and the level of radiation energy employed.

By way of further example of modifications within the scope of this invention, the means for removably attaching the reusable portion 10 to the disposable portion 50 has been described as any means which provides a secure but easily detachable connection between the reusable portion and the disposable portion, and has been exemplified as being a metal snap assembly. Other possible embodiments could include a hook-and-loop fastener tape such as "VELCRO" or an adhesive.

By way of further example of modifications within the scope of this invention, while the marker has been described as comprising a reusable portion and a disposable portion, other possible embodiments could include a marker that is fully disposable, or a marker in which any of the individual elements of those features described herein as the reusable portion and the disposable portion are disposable. For example, one fully disposable embodiment could comprise a marker in which a face of the housing opposite that side which is attached to the plate is provided with a means for removably attaching the entire integral marker, i.e., housing, sphere, and plate, to a subject. Any fo one or all of the components could be disposable.

By way of further example of modifications within the scope of this invention, an embodiment in which individual elements are disposable could comprise, for example, a marker in which the housing is disposable. The face of the housing which is perpendicular to (as depicted in FIG. 1 for the first preferred embodiment) or opposite to (as depicted in FIG. 8 for the third preferred embodiment) that side which is attached to the plate is provided with a means for removably attaching the entire assembled marker, i.e., housing, sphere, and plate, to a subject. The housing, however, is detachable from the plate and thus the sphere, and can be disposed.

By way of further example of modifications within the scope of this invention, other possible embodiments could include a configuration in which the housing is eliminated by providing the sphere itself with means for attaching to the plate, either removably or permanently, and with means for attaching to the mounting substrate, either removably, such as with a snap, or permanently. Furthermore, since it is important that first surface 31 of attenuating plate 30 be oriented substantially perpendicular to the beam path of the radiation, an adjustable embodiment could include a universal-type joint disposed between the housing and the plate so as to facilitate the proper orientation of the plate. Even another adjustable embodiment could include a universal-type joint disposed between the housing and the mounting substrate so as to facilitate even more precise orientation of the plate.

By way of further example of modifications within the scope of this invention, the method of employing the marker has been described as comprising the initial steps of affixing the mounting face 56 of the mounting substrate 51 of disposable portion 50 to a subject, then attaching reusable portion 10 to disposable portion 50 by attaching first portion 41 of the means for removably attaching to the second portion 42 of the means for removably attaching. By first attaching the reusable portion to the disposable portion, however, it would be possible to then affix the entire marker to the subject. Furthermore, by employing the fully disposable marker described above, the entire single-piece marker would simply be affixed to the subject.

By way of further example of modifications within the scope of this invention, while the marker has been described as comprising either a single sphere or two spheres in the first (FIGS. 1–6) and second (FIG. 7) preferred embodiments, respectively, another embodiment could comprise a plurality of spheres located equidistant or otherwise from one another in a single housing.

By way of further example of modifications within the scope of this invention, since the marker has been described as comprising a plurality of single-sphere reusable portions attachable to a single mounting substrate in the third preferred embodiment (FIG. 9), another embodiment could comprise a plurality of multiple-sphere reusable portions attachable to a single mounting substrate.

By way of further example of modifications within the scope of this invention, the device could be made without a plastic housing, in which case the attenuating plate would be affixed to one side of the sphere, and the female portion of the snap would be affixed to another side of the sphere for attachment to the mounting substrate.

By way of further example of modifications within the scope of this invention, the attenuating plate could be made in an L-shape with the side of the L parallel to the radiation beam having adhesive for attachment to the subject, and could be employed with one or a plurality of spheres.

By way of further example of modifications within the scope of this invention, the device could comprise a hemisphere, instead of the aforementioned sphere, with the second surface of the attenuating plate either in contact with, or in very close proximity to, the curved surface of the sphere.

By way of further example of modifications within the scope of this invention, instead of the aforementioned sphere or hemisphere, the marker could comprise a spherical or hemispherical cavity having an exterior and/or interior surface coated with radiopaque material. In the case of a hemisphere or hemispherical cavity, the plane of the flat surface of the hemisphere or hemispherical cavity must be perpendicular to the beam of radiation.

By way of further example of modifications within the scope of this invention, instead of the aforementioned sphere or hemisphere, the marker could have a shape intermediate between that of a sphere and that of a hemisphere, so long as the marker is located between the X-ray beam and the X-ray film in a manner which provides for the image on the developed film to be a full circle.

By way of further example of modifications within the scope of this invention, a different order of the steps of attaching the reference marker to the subject and removing the reference marker from the subject could be employed. That is, although the steps have been described as removably attaching reusable portion 10 to disposable portion 50 and then removably affixing mounting face 56 of the mounting substrate 51 of disposable portion 50 to a subject, another method could comprise first attaching mounting substrate 51 of disposable portion 50 to the subject, then removably attaching reusable portion 10 to disposable portion 50. Similarly, in the step of removing the reference marker from the subject, the entire assembly (i.e., the attached reusable portion 10 and disposable portion 50) can be removed as a whole, or, in a stepwise fashion, by first removing the reusable portion 10 from the disposable portion 50, and then detaching the disposable portion 50 from the subject.

By way of further example of modifications within the scope of this invention, the attenuating material could be provided by two (2) attenuating plates (one on either side of the sphere) so long as the total width of the attenuating material is sufficient to provide the necessary attenuation of the x-ray beam.

By way of further example of modifications within the scope of this invention, the marker has been described in the context of exposure to x-ray radiation, but its operation may be equally applicable to other types of imaging applications.

By way of further example of modifications within the scope of this invention, while the reference marker has been described in the context of a medical radiographic application, its operation is equally applicable to any service, e.g., scientific and industrial, which requires the accurate calculation of the degree of magnification of radiographic images.

The description and examples are intended to illustrate and not limit the scope of the invention which is defined by the full scope of the appended claims and which invention is entitled to protection within the full scope of the appended claims.

What is claimed is:

1. A radiographic reference marker to facilitate the accurate calculation of the degree of magnification or minification of radiographic images, said marker comprising:

a reusable portion and a disposable portion, said reusable portion comprising a radiopaque sphere of outside diameter $d_1$, a radiolucent plastic housing capable of frictionally but removably engaging said sphere of outside diameter $d_1$ and comprising a plate attaching face and a housing attaching face, wherein said plate attaching face comprises in a center portion thereof an aperture of a diameter capable of allowing passage therethrough of said sphere of outside diameter $d_1$, and said housing attaching face comprises a first portion of a means for removably attaching said reusable portion to said disposable portion, an attenuating plate comprising a first surface and a second surface, wherein said attenuating plate has a thickness between said first surface and said second surface sufficient to attenuate radiation, and a means for removably attaching said second surface of the attenuating plate to said plate attaching face of the plastic housing, and said disposable portion comprising a mounting substrate comprising a substrate attaching face and a mounting face, wherein said substrate attaching face comprises a second portion of said means for removably attaching said reusable portion to said disposable portion, and wherein said mounting face comprises a means for removably attaching said mounting substrate to a subject.

2. A radiographic reference marker according to claim 1, wherein said sphere has an outside diameter $d_1$ of from approximately 1 mm to 100 mm.

3. A radiographic reference marker according to claim 2, wherein said outside diameter $d_1$ is from approximately 20 to 40 mm.

4. A radiographic reference marker according to claim 1, wherein said housing is substantially cube-shaped.

5. A radiographic reference marker according to claim 1, wherein said means for removably attaching said reusable portion to said disposable portion is a snap assembly, and wherein said first portion of the means for removably attaching the reusable portion to the disposable portion is a female portion of the snap assembly, and wherein said second portion of the means for removably attaching the reusable portion to the disposable portion is a male portion of the snap assembly.

6. A radiographic reference marker according to claim 5, wherein said second portion of the means for removably attaching the reusable portion to the disposable portion is oriented such that a long axis of the male portion is perpendicular to a plane of the substrate attaching face.

7. A radiographic reference marker according to claim 1, wherein said attenuating plate has an edge length of from approximately 20 mm to 40 mm.

8. A radiographic reference marker according to claim 7, wherein said attenuating plate has an edge length of approximately 30 mm.

9. A radiographic reference marker according to claim 1, wherein said attenuating plate has a thickness of from approximately 0.5 mm to 3 mm.

10. A radiographic reference marker according to claim 9, wherein said attenuating plate has a thickness of from approximately 1 mm to 2 mm.

11. A radiographic reference marker according to claim 1, wherein said first surface of the attenuating plate comprises a portion which contains etched and/or applied designs, and/or alphabetic and/or numerical characters so as to provide an image of said designs, and/or alphabetic and/or numerical characters in the radiographic image.

12. A radiographic reference marker according to claim 1, wherein said means for removably attaching said second surface of the attenuating plate to said plate attaching face of the plastic housing is an adhesive.

13. A radiographic reference marker according to claim 1, wherein said means for removably attaching said second surface of the attenuating plate to said plate attaching face of the plastic housing comprises threaded fasteners which penetrate apertures in the attenuating plate to engage threaded cavities in the plate attaching face.

14. A radiographic reference marker according to claim 1, wherein said mounting substrate is a foam material.

15. A radiographic reference marker according to claim 1, wherein said means for removably attaching said mounting substrate to the subject is an adhesive.

16. A radiographic reference marker according to claim 1, wherein said radiation is of x-ray wavelength.

17. A radiographic reference marker according to claim 2, wherein said outside diameter $d_1$ is approximately 30 mm.

18. A radiographic reference marker according to claim 11, wherein said attenuating plate is etched so as to provide a continuous open space from said first surface through said second surface.

19. A radiographic reference marker according to claim 11, wherein said attenuating plate is etched so as to provide a continuous open space from said first surface to a point intermediate between said first surface and said second surface.

20. A radiographic reference marker according to claim 1, wherein outer portions of said first surface or said second surface of the attenuating plate are etched and/or have applied designs and/or alphabetic and/or numerical characters so as to provide an image of said designs, and/or alphabetic and/or numerical characters in the radiographic image outside the image of the circumference of the sphere.

21. A method of calculating the degree of magnification or minification of radiographic images, comprising the steps of:

by means of a reference marker comprising a reusable portion and a disposable portion, said reusable portion comprising a radiopaque sphere of outside diameter $d_1$, a radiolucent plastic housing capable of capable of frictionally but removably engaging said sphere of outside diameter $d_1$ and comprising a plate attaching face and a housing attaching face, wherein said plate attaching face comprises in a center portion thereof an aperture of a diameter capable of allowing passage therethrough of said sphere of outside diameter $d_1$, and said housing attaching face comprises a first portion of a means for removably attaching said reusable portion to said disposable portion, an attenuating plate comprising a first surface and a second surface, wherein said attenuating plate has a thickness between said first surface and said second surface sufficient to attenuate radiation, and a means for removably attaching said second surface of the attenuating plate to said plate attaching face of the plastic housing, and said disposable portion comprising a mounting substrate comprising a substrate attaching face and a mounting face, wherein said substrate attaching face comprises a second portion of said means for removably attaching said reusable portion to said disposable portion, and wherein said mounting face comprises a means for removably attaching said mounting substrate to a subject, removably attaching said reusable portion to said disposable portion by attaching said first portion of the means for removably attaching to said second portion of the means for removably attaching;

removably mounting said attached reusable portion and disposable portion by affixing said mounting face of the mounting substrate to said subject, wherein said reference marker is affixed such that said first surface of the attenuating plate and a surface of the subject to be irradiated are located substantially equidistant from an unexposed radiographic film, and such that said first surface of the attenuating plate is oriented substantially perpendicular to a beam path of radiation;

irradiating a radiographic film to produce a first image of outside diameter $d_2$ of said sphere and a second shadow image disposed concentrically around said first image;

detaching said reusable portion from said disposable portion by separating said first portion of the means for removably attaching from said second portion of the means for removably attaching;

removing said disposable portion by separating said mounting face of the mounting substrate from said subject;

measuring said first image of diameter $d_2$; and calculating a percentage of magnification or minification "M" of said first image according to the following:

$$M = \frac{d_2 - d_1}{d_1} \times 100\%.$$

* * * * *